(12) United States Patent
Claassen et al.

(10) Patent No.: US 8,420,358 B2
(45) Date of Patent: Apr. 16, 2013

(54) METHOD FOR THE COMBINED PRODUCTION OF BUTANOL AND HYDROGEN

(75) Inventors: Pieternel Claassen, Wageningen (NL); Miriam Budde, Beneden Leeuwen (NL); Geertruida De Vrije, Veenenedaal (NL); Astrid Mars, Ede (NL)

(73) Assignee: Stichting Dienst Landbouwkundig Onderzoek (NL)

( * ) Notice: Subject to any disclaimer, the term of this patent is extended or adjusted under 35 U.S.C. 154(b) by 149 days.

(21) Appl. No.: 13/001,781

(22) PCT Filed: Jun. 23, 2009

(86) PCT No.: PCT/EP2009/057802
§ 371 (c)(1),
(2), (4) Date: Jan. 27, 2011

(87) PCT Pub. No.: WO2010/000649
PCT Pub. Date: Jan. 7, 2010

(65) Prior Publication Data
US 2011/0159559 A1 Jun. 30, 2011

(30) Foreign Application Priority Data

Jul. 2, 2008 (NL) .................................... 1035651
Sep. 8, 2008 (NL) .................................... 1035905

(51) Int. Cl.
*C12P 7/16* (2006.01)
*C12P 3/00* (2006.01)

(52) U.S. Cl.
USPC .......................................... 435/160; 435/168

(58) Field of Classification Search .................. None
See application file for complete search history.

(56) References Cited

FOREIGN PATENT DOCUMENTS

WO    WO 02/006503    1/2002

OTHER PUBLICATIONS

Zverlov et al., Appld Micriobiol Biotechnol 2006 71, 587-597.*
Claasen et al.., "Non-thermal production of pure hydrogen from biomass: Hyvolution," International Journal of Hydrogen Energy, vol. 31, No. 11, Sep. 1, 2006, pp. 1416-1423, XP005601523 abstract, 4. Research plan.
De Vrije, T. et al., "Glycolytic pathway and hydrogen yield studies of the extreme thermophile *Caldicellulosiruptor saccharlyticus*," Applied Microbiology and Biotechnology, vol. 74, No. 6, Jan. 11, 2007, pp. 1358-1367, XP019513613, ISSN: 1432-0614, abstract.
Ezeji et al., "Bioproduction of butanol from biomass: from genes to bioreactors," Current Opinion in Biotechnology, vol. 18, No. 3, Jun. 8, 2007, pp. 220-227, XP022110184 ISSN: 0958-1669.
Lin et al., "Biological hydrogen production of the genus Clostridium: Metabolic study and mathematical model simulation," International Journal of Hydrogen Energy, vol. 32, No. 12, Aug. 16, 2007, pp. 1728-1735, XP022201192, abstract.
PCT Application No. PCT/EP2009/057802 filed Jun. 23, 2009 in the name of Claassen et al., International Search Report and Written Opinion mailed Aug. 27, 2009.
Van Niel, E. W. J., et al., "Distinctive properties of high hydrogen producing extreme thermophiles, *Caldicellulosiruptor saccarolyticus* and Thermotoga elfii," International Journal of Hydrogen Energy, vol. 27, No. 11-12, Nov. 1, 2002, pp. 1391-1398, XP004381765, abstract.
Van Ooteghem, S. A., et al., "Hydrogen production by the thermophilic bacterium Thermotoga neapolitana," Applied Biochemistry and Biotechnology, Spring 2002, vol. 98-100, Apr. 2002, pp. 117-189, XP008006346, ISSN: 0273-2289, abstract.
Thermotoga neapolitana, Applied Biochemistry and Biotechnology, Spring 2002, vol. 98-100, Apr. 2002, pp. 117-189, XP008006346, ISSN: 0273-2289, abstract.

* cited by examiner

*Primary Examiner* — Tekchand Saidha
*Assistant Examiner* — Md. Younus Meah
(74) *Attorney, Agent, or Firm* — Levine Bagade Han LLP

(57) ABSTRACT

The invention relates to a process for the combined production of butanol and hydrogen from biomass, comprising the steps of fermenting biomass to obtain butanol in a first reaction mixture; removing the butanol and hydrogen from the first reaction mixture to obtain effluent; and using the effluent as a substrate in a second reaction mixture in a process using low substrate concentrations, in particular a hydrogen production process. Preferably, the process using low substrate concentrations is a hydrogen production process and at least part of the end products of the hydrogen production process is removed from the second reaction mixture for obtaining an effluent that comprises organic acid, which effluent is returned to the first reaction mixture.

12 Claims, 2 Drawing Sheets

METHOD FOR THE COMBINED PRODUCTION OF BUTANOL AND HYDROGEN

Figure 1:
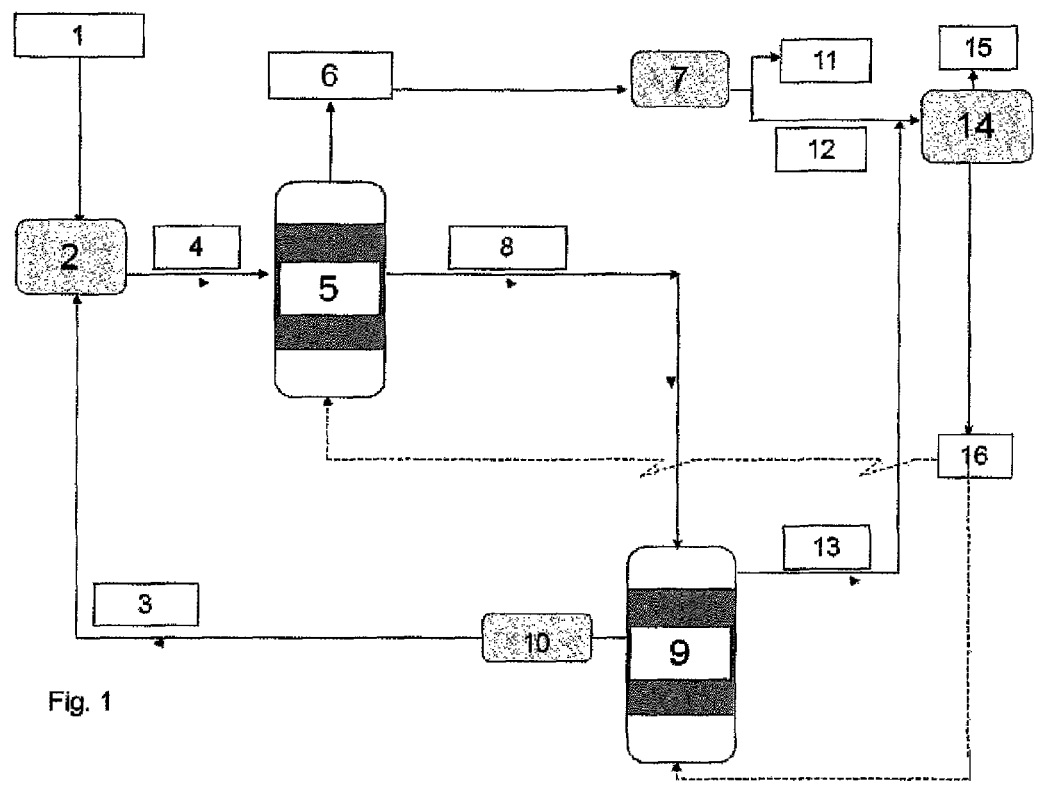

The present invention relates to a method for the combined production of butanol, in particular acetone-butanol-ethanol (ABE), and hydrogen from biomass.

Biofuels are renewable fuels made from plant matter rather than fossil fuels. Today's primary liquid biofuels are ethanol and biodiesel. Other potential biofuels are butanol and hydrogen.

Butanol is a biofuel which has superior properties with respect to bioethanol. Firstly, butanol producing, or solventogenic, bacteria ensure the conversion of hexoses as well as pentoses in contrast to the ethanol producing yeasts which only utilise hexoses. This way the full utilisation of second generation biomass comes within reach. Secondly, butanol can be applied as a fuel extender in the growing market of diesel engines, in contrast to ethanol which can be used in gasoline engines only. Furthermore, butanol can be used to prevent evaporation of ethanol in ethanol-gasoline mixtures. Finally, butanol is an interesting building block in the chemical industry.

Hydrogen is the fuel of the future where fuel cells will replace combustion engines due to inter alia the superior energy conversion efficiency. As with butanol, hydrogen is an important commodity in the chemical industry. Hydrogen is produced by many facultative and obligate anaerobic bacteria at various temperatures.

For butanol and hydrogen, applications are found in the biofuels market for automotive as well as stationary applications and in the commodity market for industrial purposes.

The quest for methods for the production of biofuel from biomass is presently based on a few thermochemical and biological processes. The intrinsic composition of the biomass governs the suitability of the process. Thermochemical processes are adequate for biomass with low water content (<20%) and high lignin content and biological (anaerobic!) processes are best suited for wet biomass and biomass with high carbohydrate content.

Within the biological processes a distinction can be made between the products, namely biogas (methane), ethanol, acetone-butanol-ethanol (ABE) and hydrogen.

ABE fermentation is a process that utilizes bacterial fermentation to produce acetone, butanol, ethanol and, to a lesser extent, iso-propanol and hydrogen from a carbohydrate containing substrate. The name ABE fermentation used in the following, stems from the past, where the emphasis was on ABE production. The process is anaerobic. It usually uses saccharolytic solventogenic clostridia.

Many clostridia produce acetone, butanol and ethanol from carbohydrates, i.e. starch, glucose, xylose and other (oligo) saccharides. Other products are hydrogen, $CO_2$, iso-propanol and butyric acid. Butanol is the product with the highest value and much of the current research is devoted to optimise the ABE fermentation towards butanol production. Presently, butanol is mainly regarded as a biofuel to be added, after derivatisation, to diesel. Additionally, butanol can be added to gasoline-ethanol mixtures to prevent evaporation of ethanol.

In a typical batch acetone-butanol-ethanol (ABE) fermentation, the process is characterized by two phases. In the first, known as the acidogenic phase, saccharides are converted to acetic and butyric acids and hydrogen accompanied by a decrease in culture pH value. In the second, known as the solventogenic phase, sugars and some of the acids are converted to acetone, butanol and ethanol, accompanied by a pH increase. Typical concentrations after batch fermentation are 15-19 g/L butanol, 4-6 g/L acetone and ≦1 g/L ethanol. Butanol is however toxic and bacteria are killed at concentrations above 20-25 g/L butanol.

A typical problem that may occur in a batch process is known as the "acid crash". When an acid crash occurs, excess acid production takes place without a significant switch to the solventogenic phase. To prevent acid crash of the bacteria, the substrate concentration is usually around 6-8% (w/v) carbohydrate. This relatively high substrate concentration is also necessary to force clostridia to ABE production during continuous fermentation.

For industrial ABE production, the main interest is in continuous fermentation. An important drawback encountered with continuous fermentation is the waste of substrate due to the requirement for high substrate concentrations to prevent the acid crash. As a result, there is a residual substrate concentration of about 2-5 g/L carbohydrate which needs to be discarded. A common option is to send this waste to a biogas fermentation unit where methane is produced.

To date the recovery of the ABE products is by distillation but there is great effort in finding alternative ways for downstream processing (membrane separation, gas stripping, etc.). The amount of $H_2$ is typically around 100 and 200 $Nm^3$ per 1000 kg carbohydrate. The production of $H_2$ is in competition with the production of butanol, i.e. more hydrogen means less butanol.

In contrast to the ABE fermentation, fermentative hydrogen production is much less studied. Interest in hydrogen production mainly stems from the expected introduction of fuel cells which need hydrogen as feedstock. Fuel cells show great promise with respect to very high efficiency in conversion of chemical energy to electrical energy (>60% as compared to 30-40% with combustion engines). As a result a switch to a hydrogen-based economy is foreseen, where part of the hydrogen needs to be derived from renewable resources to support its sustainability.

There are two distinctly different biological processes for hydrogen production, namely hydrogen production from sunlight and fermentative hydrogen production from biomass. This invention is concerned with hydrogen production from biomass.

Many micro-organisms are able to produce hydrogen from mono- and oligosaccharides, starch and (hemi)cellulose under anaerobic conditions. The anaerobic production of hydrogen is a common phenomenon, occurring during the process of anaerobic digestion. Here, hydrogen producing micro-organisms are in syntrophy with methanogenic bacteria which consume the hydrogen as soon as it is produced. In this way, hydrogen does not accumulate and methane is the end-product. By uncoupling hydrogen production from methane production, hydrogen becomes available for recovery and exploitation.

The applicant previously described the use of extreme thermophilic (temperature >70° C.) bacteria for hydrogen production and the combination of a fermentative step with a photo-heterotrophic fermentation to increase the overall yield. Mesophilic bacteria show fairly low yields of hydrogen due to the fact that these bacteria may have metabolic pathways with other, competing reduced end products (e.g. butanol or ethanol). Thermophilic bacteria show yields which can be almost twice as high (e.g. >300 $Nm^3$ per 1000 kg carbohydrate), especially when acetic acid is the only other end product.

For hydrogen producing bacteria, the optimal substrate concentration in batch fermentation for high hydrogen yield and productivity is relatively low.

According to the invention it was found that the drawbacks of the butanol production as for example in ABE fermentation, i.e. waste of substrate in the effluent, and of the hydrogen fermentation, i.e. decreased performance at high substrate concentrations, are solved by the combination of ABE and hydrogen fermentation, yielding increased efficiency in terms of high product yield from biomass at decreased cost.

The invention thus relates to a process for the combined production of butanol and hydrogen from biomass, comprising the steps of:

a) fermenting biomass to obtain butanol in a first reaction mixture;

b) removing the butanol and hydrogen from the first reaction mixture to obtain effluent; and c) using the effluent as a substrate in a second reaction mixture in a process using low substrate concentrations, in particular a hydrogen production process.

The butanol may be obtained in an ABE process, wherein it is produced in combination with acetone and ethanol. Alternatively, however, the butanol may be the main or only product of the fermentation process of step a when process parameters are used that force the production in the direction of butanol or when micro-organisms are used that produce only or mainly butanol.

The second process can be any fermentation process that uses low concentrations of sugars. This process uses the residual sugars from the first fermentation. It is however preferred according to the invention that the process is a hydrogen fermentation in which hydrogen is produced from the sugars in the effluent of the first process. Other products that can be produced from the residual sugars are acetate, lactate, pyruvate, butyrate, succinate, formate and/or ethanol. These products may be a by-product of the hydrogen production process or can be the main product of the second process.

In a preferred embodiment the end products from the second process are removed from the second reaction mixture to obtain an effluent that is returned to the first reaction mixture. For example, the metabolites, e.g. acetic acid or butyric acid, in the effluent from the hydrogen fermentation are very useful in the ABE fermentation to increase the yield of butanol. Alternatively, the metabolites in the effluent can be recovered, e.g. in the case of ethanol.

In a particular embodiment of the invention, the process of the invention thus starts with butanol production, for example by ABE fermentation of carbohydrates in the biomass. The products thus obtained are removed from the effluent and the effluent is subsequently inoculated with different bacteria for hydrogen production. The effluent leaving the hydrogen fermentor is preferably recycled to the ABE fermentor.

The clostridia that are used in the ABE process are saccharolytic solventogenic *Clostridium* species, for example selected from but not limited to the group consisting of *Clostridium acetobutylicum*, *Clostridium beijerinckii*, *Clostridium saccharobutylicum* and *Clostridium butylicum*. Many strains are commercially available (for example from DSM or from the ATCC), or are selected from own culture collections or can be produced by enrichments. For the ABE process also new ABE producing micro-organisms, including genetically modified micro-organisms, can be used.

The micro-organisms that are used in the second process, in particular for hydrogen production are preferably mesophilic, thermophilic, extreme thermophilic or hyperthermophilic anaerobic hydrogen producing species. Such micro-organisms may be selected from but are not limited to *Caldicellulosiruptor saccharolyticus*, *Caldicellulosiruptor owensensis*, *Caldicellulosiruptor Kristjanssohnii*, *Thermotoga elfii*, *Thermotoga neapolitana*, *Thermotoga maritima* and *Clostridium thermocellum*.

The advantages of the combined process are many. The residual carbohydrate of the ABE fermentation is converted to useful products such as hydrogen, acetate, lactate, pyruvate, butyrate, succinate, formate and ethanol in the hydrogen fermentation thus resulting in useful products instead of being discarded as waste.

The acid end products of the hydrogen fermentation, e.g. acetate, are re-assimilated in the ABE fermentation to increase the butanol yield and the end product ethanol adds directly to an increased product yield.

The costs for hydrogen recovery and purification are shared between the ABE fermentation and the hydrogen fermentation which leads to a cost reduction as compared to the two processes separately.

The costs for energy and/or heat demand are shared by downstream processing of the products after the ABE fermentation and energy and/or heat demand for product recovery after the hydrogen production process.

A specific advantage when employing thermophilic hydrogen bacteria at circa 70° C. is that the vegetative cells of the clostridia will lyse in the hydrogen fermentation and thus add to the supply of nitrogenous nutrients. Clostridia spores, however, remain intact or may germinate. Complete and controlled germination may be done by a temperature shock to circa 80° C. which is close to the temperature of thermophilic fermentation, enabling energy saving. The recirculation of heat-treated effluent to the ABE fermentation which runs at a lower temperature leads to a revitalization of the microbial population, thus preventing degeneration of the ABE culture.

In the combined process of the invention, two high value, diverse products are produced, namely a liquid product with acetone, ethanol, iso-propanol and mainly butanol and a gaseous product with mainly hydrogen. The butanol is a C4 building block for the chemical industry or biofuel for application in combustion engines and gaseous $H_2$ as chemical commodity or biofuel for application in fuel cells. Finally, the process of the invention is a zero waste process.

In the present application the words "ABE fermentation" are used to indicate the classic acetone-butanol-ethanol fermentation or butanol fermentation or the fermentation to produce any one of acetone, butanol and ethanol or combinations thereof.

Micro-organisms that are used for performing the various steps in the process according to the invention can be all micro-organisms that can perform the said step, either naturally occurring or genetically modified, and are in particular bacteria and yeasts.

The present invention will be further illustrated in the Example that follows. The Example is not intended to limit the invention in any way. The process of the invention is schematically illustrated in the Figures which show:

FIG. 1: a schematic overview of the process of the invention without ethanol recovery unit.

Figure 2:
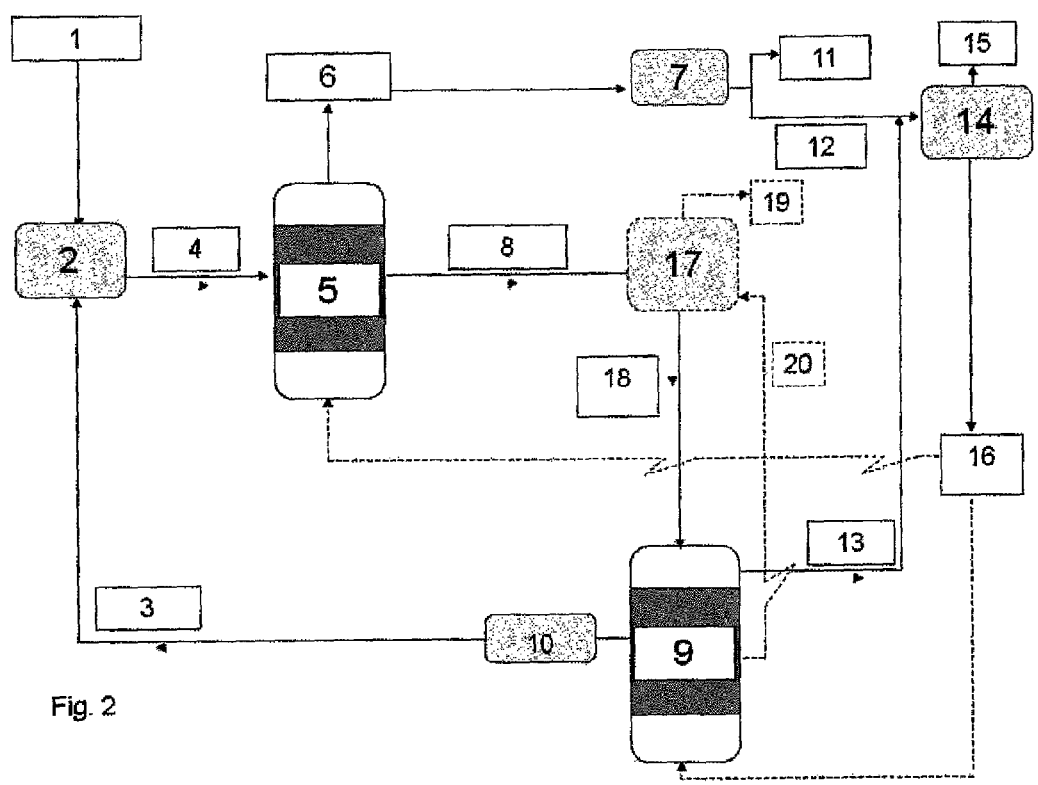

FIG. 2: a schematic overview of the process of the invention with ethanol recovery unit.

EXAMPLE

Combined Process of the Invention

In a specific embodiment the process of the invention as shown in FIG. 1 is performed with the following process parameters.

A concentrated sugar solution 1, containing 6-8% carbohydrates is loaded into a mixing unit 2. The first reaction mixture 4 that is thus obtained contains about 330 mM sugar, K,P,N salts as well as organic nitrogen and trace elements. For first inoculation, clostridial cells are added to the fermentor 5. The pH at this point is about 6-7.

This mixture 4 is fed to the ABE fermentor 5. When the process has been running for a while the sugar solution 1 can be combined with a mixture 3 that comes from the hydrogen fermentor and contains about 56 mM acetate (about pH 5-6) and germinating clostridial cells in addition to organic nitrogen and K,P,N salts (about pH 5-6).

In the ABE fermentor 5 butanol, acetone and ethanol are mainly produced. Hydrogen (about 11 L) and $CO_2$ (about 15 L) are gasses. Butanol (about 160 mM) and acetone (about 86 mM) are volatile. These compounds are removed from the reactor 5 by means of gas stripping or any other useful process and in a first product stream 6 fed to a separator or condenser 7 to separate acetone and butanol (11) from the gasses $H_2$ and $CO_2$ (12).

The second product stream 8 still contains about 33 mM sugars, K,P,N salts, as well as lysed clostridial cells and clostridial spores. The pH has dropped to about 5-6. This stream 8 is fed to a hydrogen fermentor 9. The fermentor produces about 3 L $H_2$ and about 1 L $CO_2$ (13) which are sent to the gas upgrading unit 14. The effluent is optionally heat treated in the heat treatment unit 10 to revitalize the clostridia spores contained therein and recycled to the first process as stream 3. Stream 3 still contains about 22 mM ethanol.

In the gas upgrading unit about 14 L $H_2$ (15) is recovered as well as about 16 L $CO_2$ (16). The $CO_2$ can be recycled to the hydrogen fermentor 9.

FIG. 2 shows another embodiment that comprises a additional ethanol recovery unit 17. The about 22 mM ethanol that is fed to this unit from stream 8 is recovered here. Ethanol (about 56 mM) produced in the hydrogen fermentor 9 can also be recycled to this unit to be combined with the ethanol from stream 8 resulting in stream 19 that comprises about 22+56 mM ethanol.

The invention claimed is:

1. A process for the combined production of butanol and hydrogen from biomass, comprising the steps of:
    a) fermenting biomass to obtain butanol in a first reaction mixture;
    b) removing the butanol from the first reaction mixture to obtain effluent; and
    c) using the effluent as a substrate in a second reaction mixture in a process using low substrate concentrations, in particular a hydrogen production process.

2. The process as claimed in claim 1, characterized in that the butanol is produced in an :acetone-butanol-ethanol (ABE) production process.

3. The process as claimed in claim 1, characterized in that the process using low substrate concentrations is a hydrogen production process and at least part of the end products of the hydrogen production process is removed from the second reaction mixture for obtaining an effluent that comprises an organic acid which effluent is returned to the first reaction mixture.

4. The process as claimed in claim 3, characterized in that, the organic acid is acetate or butyrate.

5. The process as claimed in claim 2, characterized in that, the ABE production process uses micro-organisms, including genetically modified microorganisms.

6. The process as claimed in claim 2, characterized in that the acetone-butanol-etlianol (ABE) production process uses solvemogenic clostridia species, preferably selected from the group consisting of *Clostridiuni acetobutylicum, Clostridium beijerinckii, Clostridium saccharobutylicum* en *Clostridium butylicum.*

7. The process as claimed in claim 1 characterized in that the hydrogen production process uses mesophilic, thermophilic, extreme thermophilic or hyperthermophilic bacteria, including genetically modified microorganisms.

8. The process as claimed in claim 7, characterized in that the bacteria are selected from the group consisting of *Caldicellulosiruptor saccharolyticus, Caldicellulosiruptor owensensis, Caldicellulosiruptor Kristjanssohnii, Thermotoga elfii, Thermotoga neapolitana, Thermotoga maritima* en *Clostridium thermocellum.*

9. The process as claimed in claim 1, the effluent of step b) comprises a residual concentration of carbohydrates from 2-10 g/I.

10. The process as claimed in claim 1, characterized in that step c) comprises a thermophilic fermentation which is applied for revitalization of a clostridium population in an ABE production.

11. The process as claimed in claim 1, characterized in that the process further comprises recovery of ethanol from the effluent of the process of step b).

12. The process as claimed in claim 1, characterized in that the process further comprises recovery of ethanol from the effluent of the process of step c).

* * * * *